(12) United States Patent
Stenton (10) Patent No.: US 7,909,808 B2
(45) Date of Patent: Mar. 22, 2011

(54) DUAL-ENDED APPLICATOR FOR DISPENSING TWO FLUIDS

(75) Inventor: Richard Stenton, Horrabridge (GB)

(73) Assignee: Medlogic Global Limited, Plymouth, Devon (GB)

( * ) Notice: Subject to any disclaimer, the term of this patent is extended or adjusted under 35 U.S.C. 154(b) by 1694 days.

(21) Appl. No.: 10/460,646

(22) Filed: Jun. 13, 2003

(65) Prior Publication Data

US 2004/0254561 A1 Dec. 16, 2004

(51) Int. Cl.
*A61M 31/00* (2006.01)
(52) U.S. Cl. .................................. 604/500
(58) Field of Classification Search ........... 604/500
See application file for complete search history.

(56) References Cited

U.S. PATENT DOCUMENTS

| | | | |
|---|---|---|---|
| 2,784,127 A | 3/1957 | Joyner et al. | |
| 3,527,224 A | 9/1970 | Rabinowitx | |
| 3,591,676 A | 7/1971 | Hawkins et al. | |
| 3,667,472 A | 6/1972 | Halpern | |
| 3,995,641 A | 12/1976 | Kronenthal et al. | |
| 4,035,334 A | 7/1977 | Davydov et al. | |
| 4,444,933 A | 4/1984 | Columbus et al. | |
| 4,650,826 A | 3/1987 | Waniczek et al. | |
| 5,480,935 A | 1/1996 | Greff et al. | |
| 5,582,596 A | 12/1996 | Ishihara et al. | |
| 5,962,010 A * | 10/1999 | Greff et al. | 424/443 |
| 5,975,367 A | 11/1999 | Alcone et al. | |
| 5,976,102 A * | 11/1999 | Epstein | 604/35 |
| 5,998,472 A | 12/1999 | Berger et al. | |
| 6,283,933 B1 | 9/2001 | D'Alessio et al. | |
| 6,475,502 B1 | 11/2002 | Lee et al. | |
| 6,547,467 B2 | 4/2003 | Quintero | |
| 6,592,281 B2 | 7/2003 | Clark et al. | |
| 6,595,940 B1 | 7/2003 | D'Alessio et al. | |
| 2003/0080151 A1 | 5/2003 | D'Alessio et al. | |

FOREIGN PATENT DOCUMENTS

| | | |
|---|---|---|
| EP | 0858755 | 8/1998 |
| JP | 01025843 | 1/1989 |
| WO | WO 95/31138 | 11/1995 |

OTHER PUBLICATIONS

Second Collegiate Edition, American Heritage Dictionary, 1976, p. 121.*
Burns et al., "Using Tissue Adhesive for Wound Repair: A Practical Guide to Dermabond," in American Family Physician, vol. 61, No. 5, Mar. 1, 2000, hand numbered 1-7.*

* cited by examiner

*Primary Examiner* — Blessing M Fubara
(74) *Attorney, Agent, or Firm* — Antoinette F. Konski; Foley & Lardner LLP (57) ABSTRACT

An applicator for dispensing two separate tissue adhesives includes a generally elongate body having two distinct interior regions, each containing one of the two tissue adhesives. Hinged levers associated with each region selectively force the expulsion of the adhesive from the end portions of the applicator in response to application of force by the operator.

11 Claims, 7 Drawing Sheets

DUAL-ENDED APPLICATOR FOR DISPENSING TWO FLUIDS

BACKGROUND OF THE INVENTION

1. Field of the Invention

This invention is directed to improved applicators and methods for applying adhesives, and more particularly for medical adhesives. It provides for the accurate application of small amounts of adhesive in specific spots to create strong point bonds analogous to spot welds. In addition, it allows for the application of a sealant layer over the area that has been bonded, thereby permitting flexible sealing of the adhered surfaces.

It is expected to be especially useful in closure of long wounds in mammalian tissue, such as surgical incisions or traumatic lacerations.

2. State of the Art

Surgical incisions or lacerations are currently closed by sutures, staples, adhesive strips, or liquid tissue adhesives. Sutures, staples, and adhesive strips have been widely used for many years, and tissue adhesives have recently received significant acceptance with the launch of DERMABOND™ by J&J in the USA, and LiquiBand and other products in Europe. Tissue adhesives are typically applied as a thin line or wide swath along the line of the wound after the skin edges have been brought together (approximated). The edges of the wound then have to be held together while the adhesive sets. One of the advantages of tissue adhesives over the older forms of wound closure is that they both close and also seal the wound to allow fluid retention and keep out infectious agents. This may allow the patient to bathe almost immediately without fear of blood loss or infection.

A tissue adhesive is typically a low viscosity liquid that has a high affinity for tissue and wets it very easily. The applicators are typically tubes or ampoules with wide tips that have to be squeezed by the user to expel the adhesive for application. The release of the low viscosity fluid is frequently not well controlled, and can lead to flow of the adhesive into unwanted areas where it can cause unwanted adhesions. There have been many reported cases where adhesive has run into a patient's eyes or where the practitioner had glued his or her glove or instruments to the patient because of poor control of the application of the adhesive. In addition to this, strong tissue adhesives tend to be inflexible, whereas flexible tissue adhesives tend to give weaker bonds. Therefore wound closure tissue adhesives have tended to be a compromise between flexibility and bond strength.

Typical of the state of the art is DERMABOND™, which is manufactured by Closure Corporation and sold by the Ethicon Division of J&J. This product is 2-octyl cyanoacrylate presented in a plastic applicator which contains a crushable glass ampoule. The end of the applicator contains a porous spherical tip approximately {fraction (5/16)}" in diameter through which the adhesive is applied after the internal glass ampoule is crushed. The adhesive is low viscosity, typically less than 10 cps, and rapidly wets mammalian skin, allowing it to run freely across the skin. Application of tissue adhesive from this tip is difficult to control. The directions of DERMABOND™ instruct the user to "Approximate wound edges with gloved fingers or sterile forceps. Slowly apply the liquid DERMABOND™ adhesive in multiple (at least 3) thin layers to the surface of the approximated wound edges using a gentle brushing motion. Wait approximately 30 seconds between applications or layers. Maintain manual approximation of the wound edges for approximately 60 seconds after the final layer." The adhesive layer formed by this method is typically ¼ inch or more wide and quite thick due to the application of three layers. The width and thickness of this layer make the layer stiff despite the fact that 2-octyl cyanoacrylate has a lower modulus than the lower homologues such as ethyl, butyl and hexyl cyanoacrylate. The technique does not lend itself to closure of incisions or lacerations longer than a few centimeters because the wound edges have to be entirely approximated before applying the layers of adhesive.

More recently, some practitioners have adopted a procedure of "spot welding" a wound with tissue adhesives by applying tiny spots of adhesive at intervals along a wound. In this fashion they only have to approximate the wound edges at the spot they are joining and they can close much longer wounds. Once the wound has been appropriately closed, the practitioner can seal the wound by running a thin line of tissue adhesive along the length of the wound. This advance in wound closure technique is possible because of strong, fast-setting adhesives, which can be applied accurately in very small quantities. However, the strong, fast-setting adhesives tend to be stiff and the sealant line formed from this adhesive may render the wound uncomfortable.

BRIEF SUMMARY OF THE INVENTION

In accordance with the invention, an applicator is provided having first and second end portions from which first and second distinct fluids are dispensed. The applicator includes a housing assembly defining first and second separate regions adapted to contain the first and second distinct fluids, the first and second regions being in fluid communication with the exterior of the applicator at said first and second end portions of the applicator, respectively, and being separated from each other such that the first and second fluids do not intermix within the housing assembly. The applicator further includes a first pressure device for imparting sufficient pressure to the first fluid to cause egress of same out of the applicator at said first end portion.

BRIEF DESCRIPTION OF THE SEVERAL VIEWS OF THE DRAWINGS

Many advantages of the present invention will be apparent to those skilled in the art with a reading of this specification in conjunction with the attached drawings, wherein like reference numerals are applied to like elements.

DETAILED DESCRIPTION OF THE INVENTION

Figure 1A:
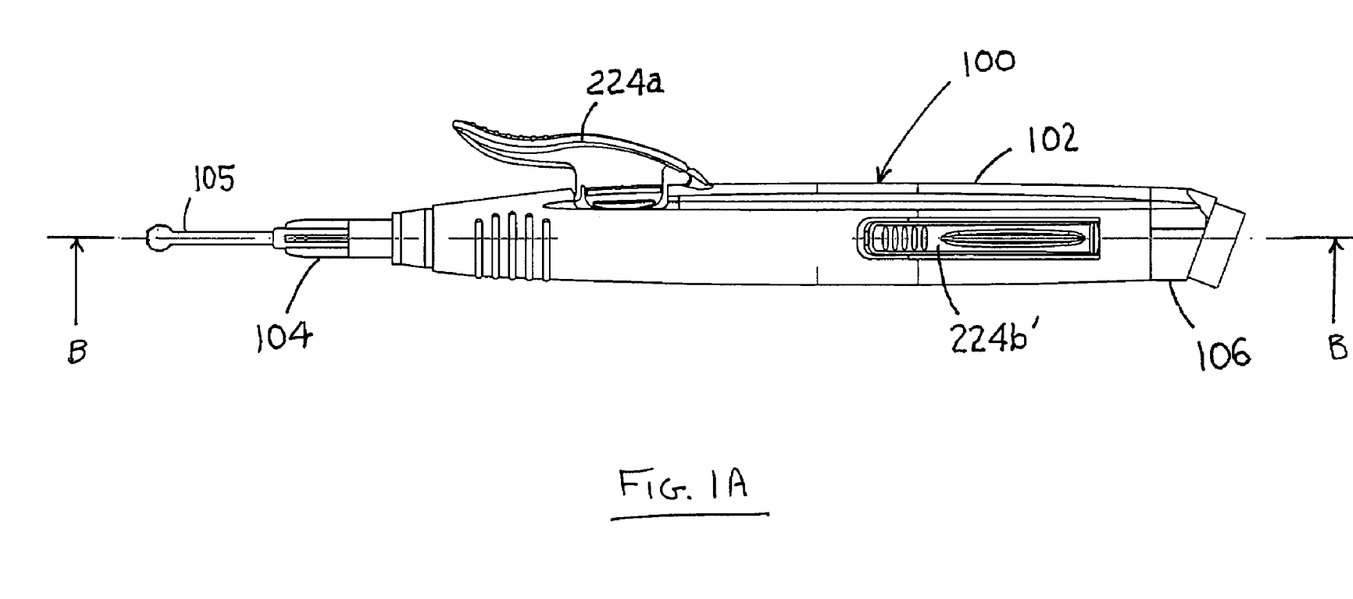
FIG. 1A is a left elevational view of the applicator in accordance with the invention.
Figure 1B:
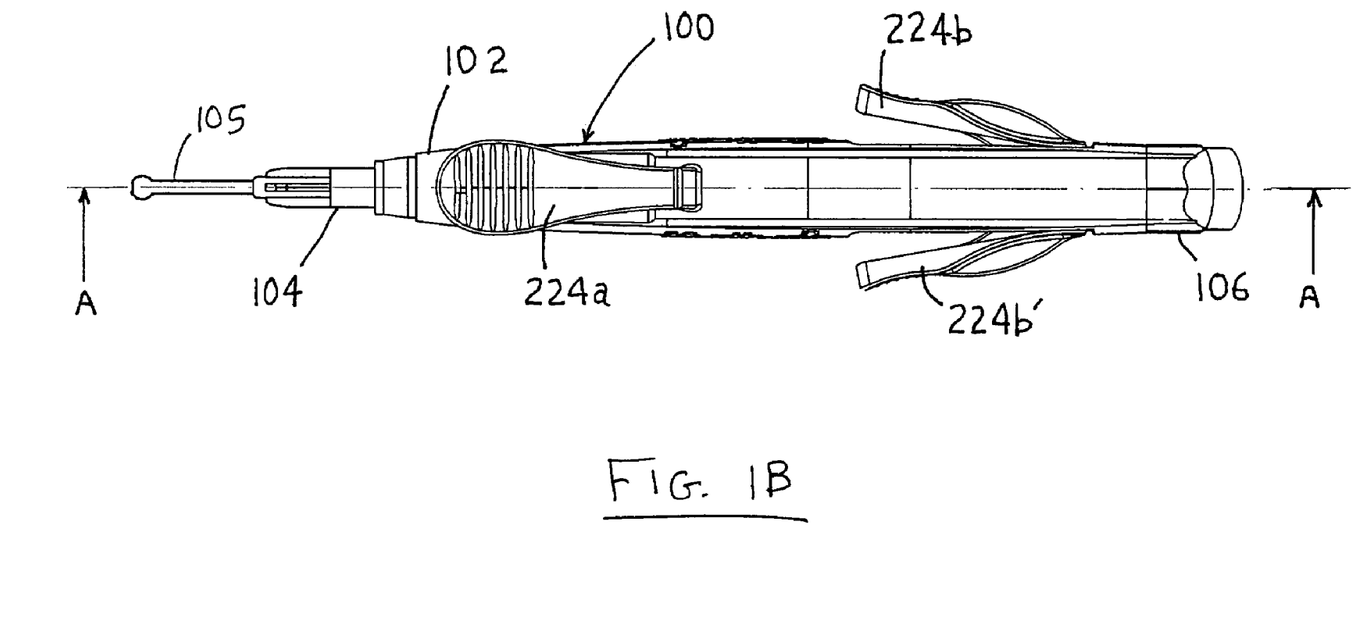
FIG. 1B is a top view of the applicator of FIG. 1A.

FIGS. 1A and 1B are respectively a left side elevational view and a top view of an applicator 100 in accordance with the invention. Applicator 100 comprises generally a housing assembly 102, and has first and second end portions, 104 and 106, respectively. Applicator 100 is designed to segregate two masses of fluid contained therein (not shown), and to selectively dispense the fluids from end portions 104 and 106.

Figure 2:
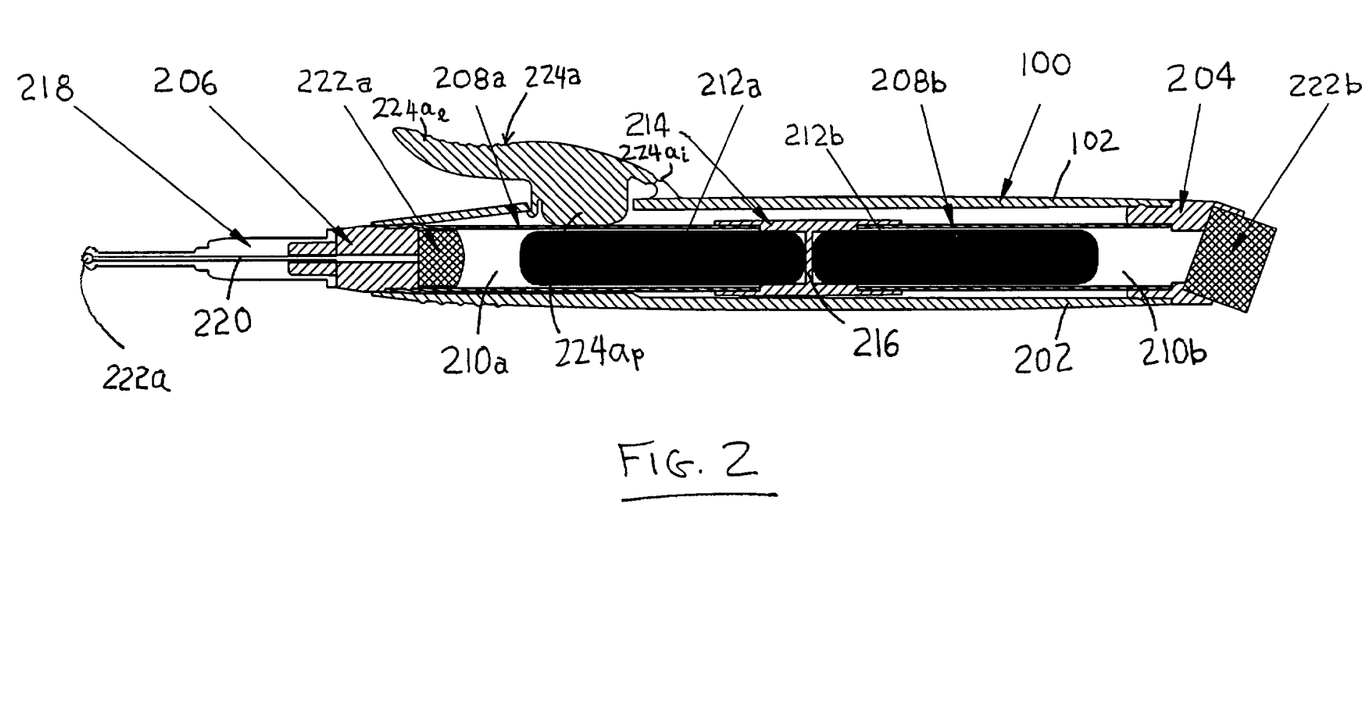
FIG. 2 is a cross-sectional view of the applicator of FIG. 1B, taken along line A-A.
Figure 3:
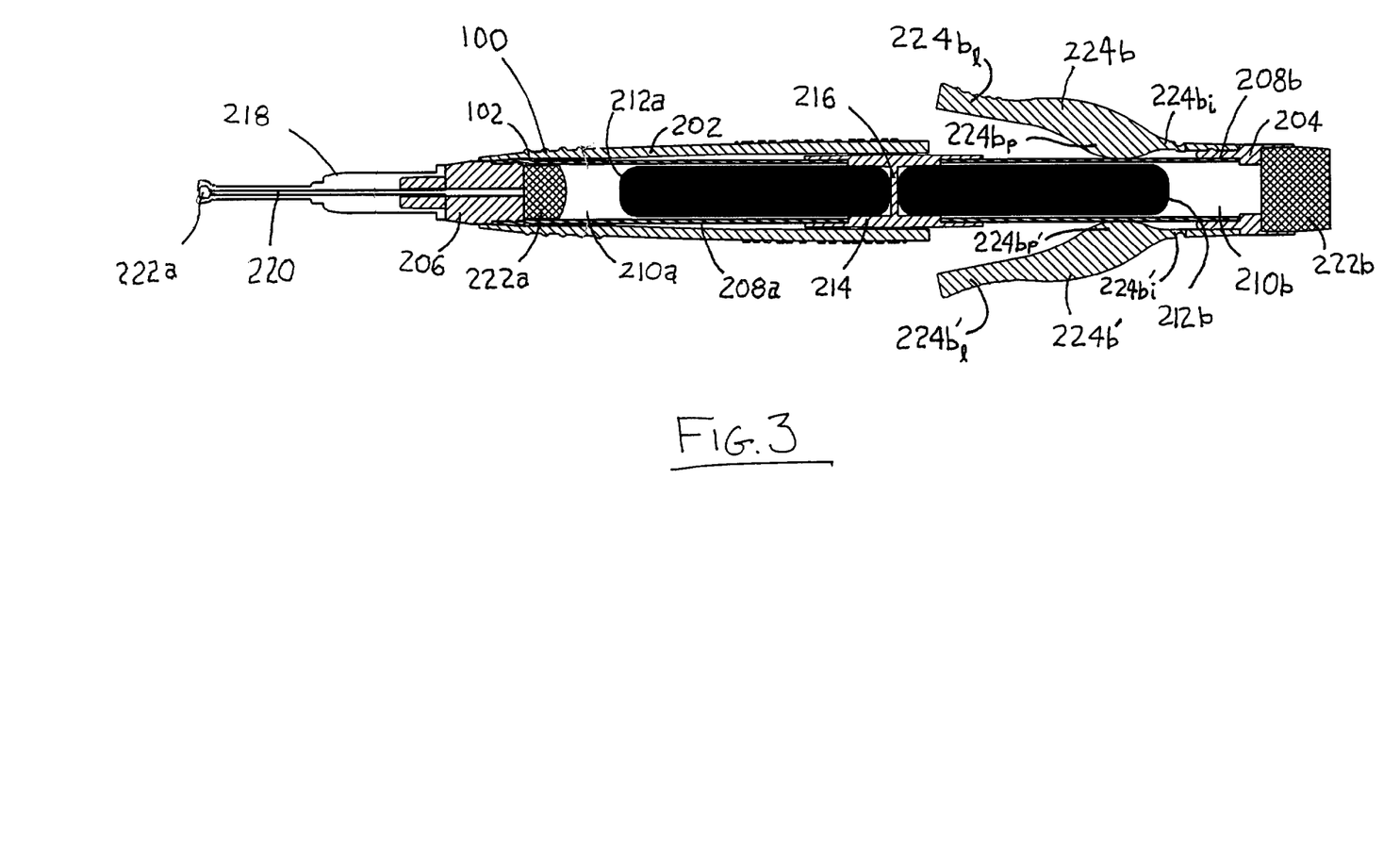
FIG. 3 is a cross-sectional view of the applicator of FIG. 1A, taken along line B—B.

FIGS. 2 and 3 are cross-sectional views of applicator 100 taken along lines A-A and B-B in FIGS. 1B and 1A, respectively. Housing assembly 102 includes a generally elongate body 202 capped at one end by annular structure 204 and at the other end by an end cap 206. Housing assembly 102 defines a chamber in which are disposed a pair of deformable tubes 208a and 208b, each at least partially containing within an interior region (210a, 210b) thereof a hermetically sealed ampoule (212a, 212b) of a suitable adhesive. Preferably, ampoule 212a contains a strong, fast-setting adhesive such as n-butyl cyanoacrylate and pentyl cyanoacrylate, while ampoule 212b contains a more flexible tissue adhesive such as octyl cyanoacrylate or hexylcyanoacrylate. Other types of adhesives may also be used, as detailed below. It will also be understood that in some applications, the two ampoules 212a and 212b would contain the same adhesive compound.

Regions 210a and 210b are separated from each other such that intermixing of the contents of ampoules 212a and 212b will not occur when the ampoules are unsealed, such as by crushing, in the manner detailed below. Separation is effected primarily by a center joiner 214 serving to retain the ends of tubes 208a and 208b, and configured as a generally tubular structure with a central impermeable barrier 216 formed therein. Retaining the opposite end of tube 208b is annular structure 204, which serves as a conduit for fluid communication between region 210b and the exterior of applicator 100.

Figure 2A:
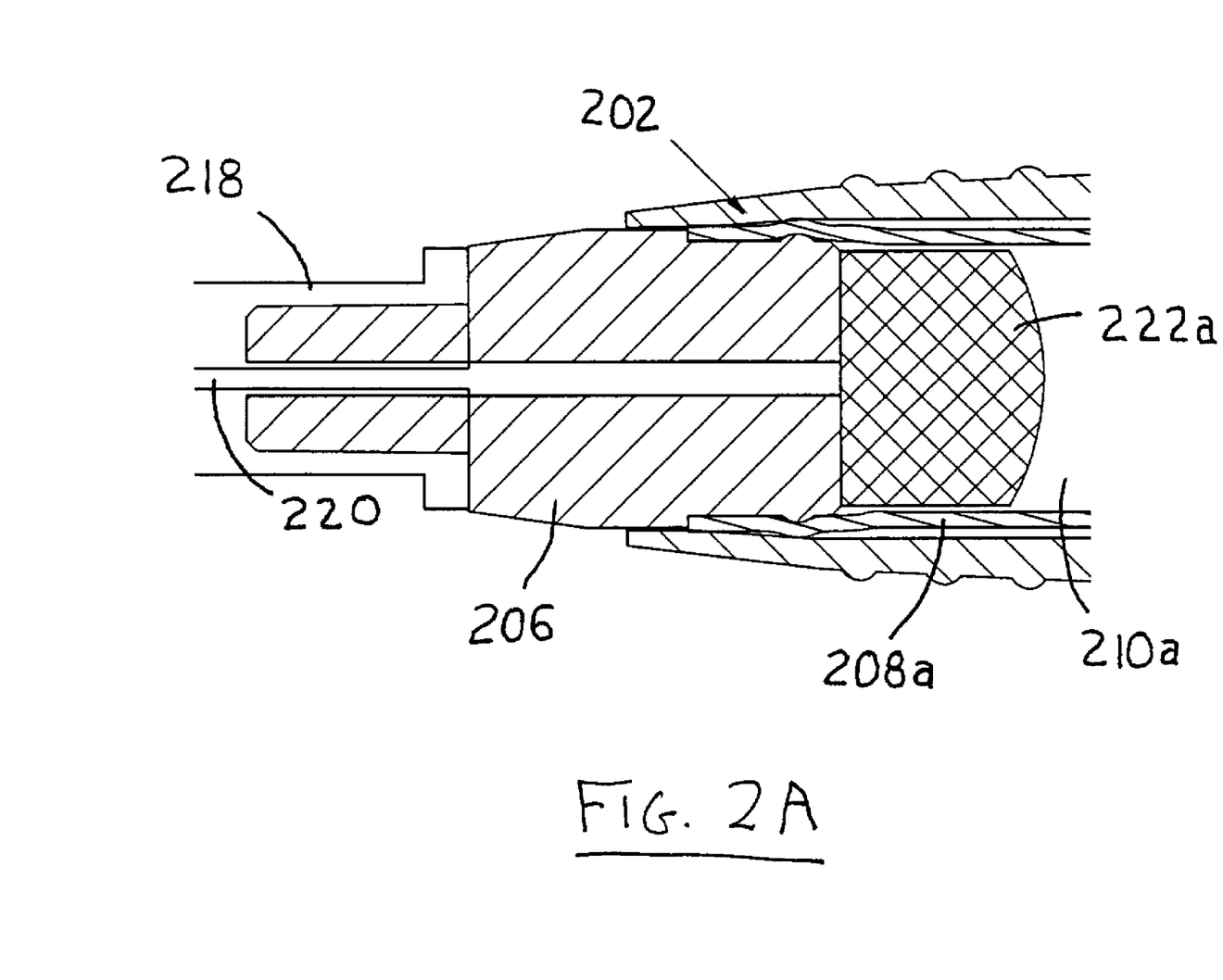
FIG. 2A is an expanded view of a portion of FIG. 2.

Similarly, tube 208a is supported at its opposite end by end cap 206, with tube 208a fitting between the exterior of end cap 206 and the interior of body 202, as detailed in FIG. 2A. Abutting end cap 206 is a nozzle 218, which is provided with a central channel, in registry with a central channel formed in end cap 206. These central channels form a fluid conduit 220, permitting fluid communication between region 210a and the exterior of applicator 100. Filters 222a and 222b are disposed in the fluid flow paths between interior regions 210a and 210b and the exterior of applicator 100, and serve to prevent passage of pieces of ampoules 212a and 212b to the exterior of applicator 100, without hindering the passage of the adhesives contained in the ampoules. A spherical, microporous tip 222a is also provided, in the region of the end of conduit 220, to aid in the spreading of the fluid.

Pressure devices, such as hinged levers 224a, 224b and 224b', are provided in order to selectively and controllably impart force from an operator's hand (not shown) to tubes 208a and 208b, thereby unsealing ampoules 212a and 212b by crushing them, and ultimately forcing the egress of their contents out of applicator 100.

Hinged levers 224a, 224b and 224b' have respective leveraging portions (224a$_l$, 224b$_l$, and 224b$_l$') which engage the operator's fingers to receive therefrom inwardly-directed pressure—that is, pressure in the direction of the applicator 100. Hinged levers 224a, 224b and 224b' also have respective plunger portions (224a$_p$, 224b$_p$ and 224b$_p$') which engage tubes 208a and 208b—directly as shown or indirectly through some other known force-transferring mechanism—and convey the force from the operator's fingers to the tubes, deforming the tubes and crushing fluid-containing ampoules 212a and 212b therein. To facilitate the hinged action, hinged levers 224a, 224b and 224b' are rotatably-attached to housing assembly 102, preferably to elongate body 202, at points 224a$_i$, 224b$_i$ and 224b$_i$', respectively. The attachment is preferably by way a flexible connective bridge, of integral material with the lever and/or elongate body 202. Alternatively, a conventional hinge-type arrangement (not shown) may be provided for that purpose. The plunger portions 224a$_p$, 224b$_p$ and 224b$_p$' of levers 224a, 224b and 224b' are shaped such that their contours and volume at the point of interaction with tubes 208a and 208b allow for good control of the volume of fluid being squeezed out of regions 210a and 210b during the inwardly-directed motion of the levers.

The materials of the components of applicator 100 are selected to be compatible with each other, and with the adhesives contained in ampoules 212a and 212b, particularly for those components intended to come into contact with the adhesives. Biocompatibility is also important, to reduce the risk of injury and/or toxicity to the patient. When the adhesives are cyanoacrylates, materials that are non-reactive with cyanoacrylates would be selected. Polymeric materials can be used for the components of the applicator 100, so long as the polymeric materials are compatible with adhesives (that is, the applicator components will not readily degrade in the adhesives, the adhesives will not degrade the applicator components, and the applicator components will not effect polymerization of any prepolymer). In this regard, it is preferred to use high density polyethylene or polypropylene in the applicator components because of their inertness in the presence of the adhesive compositions described herein. Other materials compatible with the adhesive compositions can be readily determined by the skilled artisan and include, for example, other polyolefins, such as, polyethylene (80A-80D), polyester polyether block copolymer (30D-80D), Alcryn (chlorinated polyolefin) (60A-80A), Pebax (polyamide polyether block copolymer) (25D-70D); fluoropolymers, such as, PTFE (polytetrafluoroethylene, such as Teflon™), perfluoroalkoxy resin, fluorinated ethylene propylene polymers, ETFE, and SEBS (styrene ethylene butadiene styrene); silicones; interpenetrating networks of silicone; nylons (6/6, 6/10, and 6/12) and polyamide.

Figure 4:
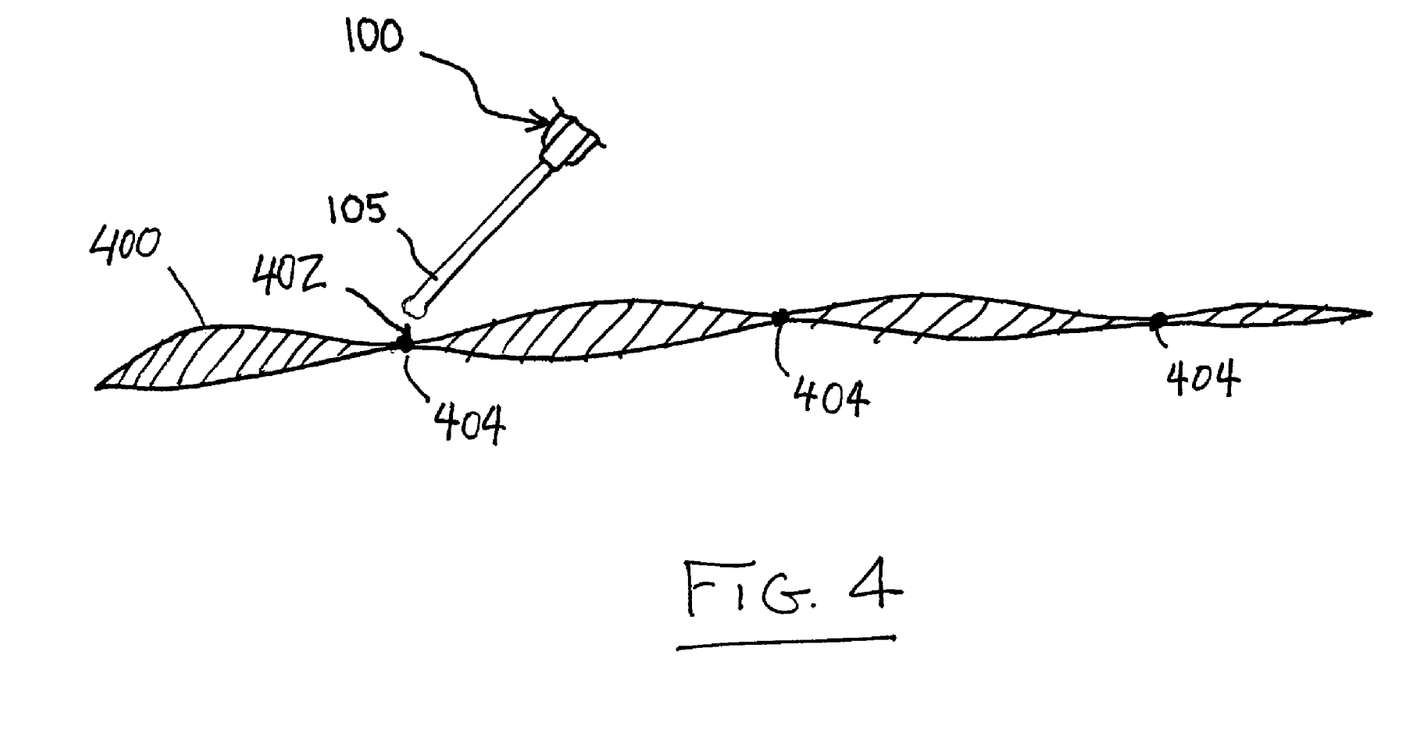
FIG. 4 is a view showing the use of the applicator of the invention to apply a strong, fast-setting adhesive to an incision.

As seen from FIG. 4, and with reference to FIG. 2, during use, in order to close an incision 400 following surgery, tip 105 of applicator 100 is brought into close proximity to the incision, and hinged lever 224a (FIG. 2) is depressed by the operator (not shown) with sufficient force to break ampoule 212a and cause a small amount of the strong, fast-setting adhesive 402 contained therein to flow into region 210a, through filter 222a and channel 220, to the exterior of applicator 100. The strong, fast-setting adhesive is applied in spots 404 to the edges of the incision, in a manner analogous to spot welding, to provide a strong bond to retain the edges together at least long enough to apply the more flexible tissue adhesive contained in ampoule 212b.

Figure 5:
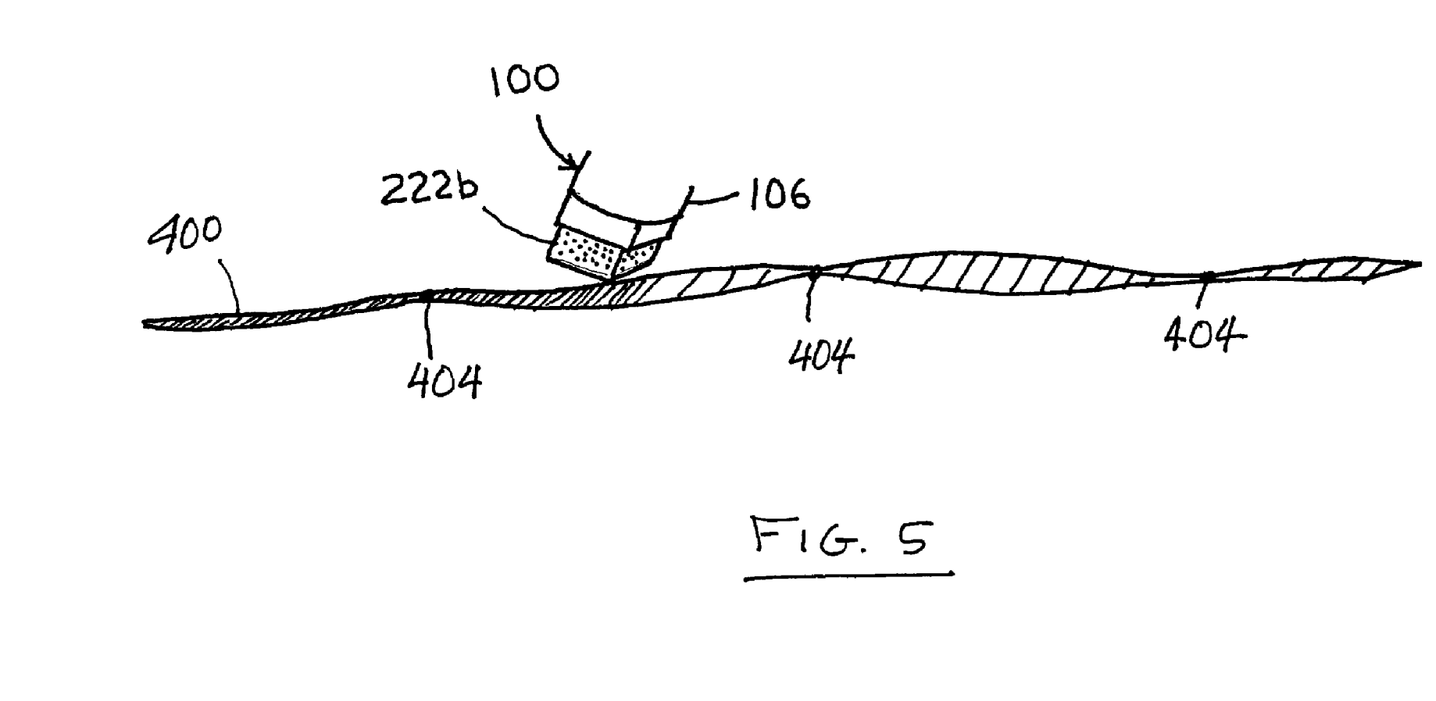
FIG. 5 is a view showing the use of the applicator of the invention to apply a more flexible tissue adhesive to the incision of FIG. 4.

Application of the more flexible tissue adhesive from ampoule 212b is illustrated in FIG. 5 and takes place by bringing end portion 106 of applicator 100 into close proximity to the incision 400, either before or after ampoule 212b is broken by action of hinged levers 224b and 224b'. Sufficient force is applied to hinged levers 224b and 224b' to expel the flexible tissue adhesive from region 210b, through filter 222b, and out of the applicator 100. Filter 222b is run along the incision 400 while sufficient pressure is applied to hinged levers 224b and 224b' to cover the area of the incision and provide complete closure thereof.

Cyanoacrylate Adhesive Compositions:

The adhesives fluids that may be applied by the applicator of the present invention may be comprised of a wide variety of cyanoacrylate adhesive formulations. It is to be understood, however, that the present invention is not limited to any particular type of adhesive and any suitable medical (or non-medical) adhesive can be used. Generally, the first ampoule or reservoir will contain a stronger bonding and less flexible cyanoacrylate adhesive composition, such as n-butyl cyanoacrylate, while the second reservoir will hold a more flexible tissue adhesive, such as an octyl or hexyl cyanoacrylate.

In accordance with an optional preferred aspect of the present invention, both reservoirs will contain cyanoacrylate adhesive formations. Preferably, the cyanoacrylate compositions used comprise cyanoacrylate prepolymer compositions that can be applied as a liquid/gel to the skin surface. Optionally, the cyanoacrylate prepolymers can include therapeutic agents such as analgesics, anti-inflammatory agents, antimicrobial agents, and the like.

Preferably, the polymerizable cyanoacrylate prepolymers comprise cyanoacrylate esters that, in monomeric form, are represented by formula I:

wherein
R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

wherein
each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxyl, chloro, bromo, nitro, alkyl of 1 to 4 carbon atoms, and alkoxy of from 1 to 4 carbon atoms.

More preferably, in the cyanoacrylate esters of formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. Mixtures of such compounds can also be employed as disclosed by Berger, et al., U.S. Pat. No. 5,998,472, which is incorporated herein by reference in its entirety. For the stronger, less flexible adhesive, R is preferably ethyl, butyl or pentyl, thereby giving the resulting polymer film a higher modulus. For the more flexible adhesive, R is preferably hexyl or octyl. In one, highly preferred embodiment, the first reservoir contains an n-butyl cyanoacrylate ester and the second reservoir contains an octyl cyanoacrylate ester.

It is to be understood that the term "polymerizable cyanoacrylate esters" refers to polymerizable formulations comprising cyanoacrylate monomers or polymerizable oligomers which, in their monomeric form, are preferably compounds represented by formula I as described above.

The polymerizable cyanoacrylate esters described herein rapidly polymerize in the presence of water vapor or tissue protein, and the n-butyl-cyanoacrylate bonds to mammalian skin tissue without causing histotoxicity or cytotoxicity.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Optionally, the cyanoacrylate compositions applied by the present applicator can include a "biocompatible plasticizer". As used herein, the term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and $C_2$-$C_4$-acyl tri-n-hexyl citrates.

Optionally as well, the cyanoacrylate composition applied by the present applicator can include an "antimicrobial agent". As used herein, the term "antimicrobial agent" refers to agents which destroy microbes (i.e., bacteria, fungi, yeasts and viruses) thereby preventing their development and their pathogenic action.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of a compatible antimicrobial agent. Such compositions preferably comprise from about 0.1 to about 30 and preferably about 0.5 to about 10 weight percent of the compatible antimicrobial agent either as a solution or as a suspension based on the total weight of the composition. Compatible antimicrobial agents are those that are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. Pat. No. 6,475,502, which discloses compositions of cyanoacrylate/povidone-iodine complexes, and U.S. Application Publication No. US 2005-0042196, which discloses compositions of cyanoacrylate esters and phenol. All three disclosures are incorporated herein by reference in their entirety.

The use of a compatible antimicrobial agent in the compositions permits the agent to be released from the polymeric film thereby reducing microbial growth adjacent to the film.

Other medicaments suitable for use in conjunction with the cyanoacrylate compositions include corticoid steroids such as described by Greff, et al. in U.S. Pat. No. 5,962,010 which is incorporated herein by reference in its entirety and analgesic compounds such as lidocaine. The former reduces inflammation whereas the latter reduces pain. Combinations of a steroid with an analgesic are also covered.

The above are exemplary modes of carrying out the invention and are not intended to be limiting. It will be apparent to those of ordinary skill in the art that modifications thereto can be made without departure from the spirit and scope of the invention as set forth in the following claims.

The invention claimed is:

1. An applicator having first and second end portions from which first and second distinct fluids are dispensed, the applicator comprising:
    a housing assembly defining first and second separate regions adapted to contain the first and second distinct fluids, the first and second regions being in fluid communication with the exterior of the applicator at said first and second end portions of the applicator, respectively, and being separated from each other such that the first and second fluids do not intermix within the housing assembly wherein the first and the second end portions are at an opposite end of the applicator;
    a first pressure device which is a first hinged lever having a first plunger portion for imparting sufficient pressure to the first fluid selectively to cause egress of same out of the applicator at said first end portion;
    a second pressure device which is a second hinged lever having a second plunger portion for imparting sufficient pressure to the second fluid selectively to cause egress of same out of the applicator at said second end portion; and
    wherein said first and second fluids are cyanoacrylate prepolymers.

2. The applicator of claim 1, further comprising a first hermetically sealed ampoule disposed in the first region and containing the first fluid, the first lever operating to destroy the integrity of the first ampoule such that the first fluid escapes therefrom.

3. The applicator of claim 2, further comprising a first filter for impeding the flow of broken pieces of the first ampoule out of the applicator.

4. The applicator of claim 1, further comprising a second hermetically sealed ampoule disposed in the second region and containing the second fluid, the second lever operating to destroy the integrity of the second ampoule such that the second fluid escapes therefrom.

5. The applicator of claim 4, further comprising a second filter for impeding the flow of broken pieces of the second ampoule out of the applicator.

6. The applicator of claim 1, wherein the cyanoacrylate prepolymer of the first fluid is a fast-setting strong prepolymer adhesive and the cyanoacrylate prepolymer of the second fluid is a prepolymer adhesive capable of forming a flexible sealant layer.

7. The applicator of claim 1, wherein the cyanoacrylate prepolymer of the first fluid comprises n-butyl cyanoacrylate.

8. The applicator of claim 1, wherein the cyanoacrylate prepolymer of the second fluid comprises octyl cyanoacrylate.

9. The applicator of claim 1, wherein the cyanoacrylate prepolymer of the second fluid is a blend of butyl and octyl cyanoacrylate.

10. The applicator of claim 1, wherein the cyanoacrylate prepolymer of the second fluid is a blend of butyl and decyl cyanoacrylate.

11. The applicator of claim 1, wherein said first end portion comprises a spherical microporous tip and said second end portion comprises a dispensing filter.

* * * * *